United States Patent [19]

Schinhammer

[11] 3,949,478
[45] Apr. 13, 1976

[54] PROCESS AND APPARATUS FOR FITTING ORTHODONTIC BRACKETS TO TEETH

[75] Inventor: Karl Schinhammer, Letmathe, Germany

[73] Assignee: Firma Scheu-Dental, Inhaber Rudolf Scheu Herstellung und Vertrieb von Dentalbedarf, Letmathe, Germany

[22] Filed: Dec. 27, 1974

[21] Appl. No.: 536,984

[52] U.S. Cl. .................................. 32/14 A; 32/71
[51] Int. Cl.² ........................................ A61C 7/00
[58] Field of Search ...... 32/14 R, 14 A, 14 B, 40 R, 32/70, 71, 1

[56] References Cited
UNITED STATES PATENTS

| | | | |
|---|---|---|---|
| 3,277,576 | 10/1966 | Kraft | 32/40 R |
| 3,316,640 | 5/1967 | Kesling | 32/14 B |
| 3,436,829 | 4/1969 | Jermyn | 32/40 R |
| 3,439,421 | 4/1969 | Perkowski | 32/14 A |
| 3,461,562 | 8/1969 | Cooper | 32/40 R |
| 3,469,316 | 9/1969 | Stern et al. | 32/40 R X |
| 3,510,946 | 5/1970 | Kesling | 32/14 C |
| 3,552,018 | 1/1971 | Lahn | 32/40 R |
| 3,738,005 | 6/1973 | Cohen et al. | 32/14 B |
| 3,842,503 | 10/1974 | Wildman | 32/14 A |

Primary Examiner—Louis G. Mancene
Assistant Examiner—Jack Q. Lever
Attorney, Agent, or Firm—Toren, McGeady and Stanger

[57] ABSTRACT

Orthodontic brackets are fitted to teeth to be treated by making a first positive jaw model from which the model teeth are replaceably removable. The model teeth are subsequently placed into a second jaw model containing pliable material which enables the teeth to be displaced into a desired predetermined orientation, which is the orientation ultimately desired for the teeth to be treated. With the model teeth in this orientation, brackets are fitted to the model teeth and utilizing procedures which involve making a negative mold of the model teeth with the attached brackets, the brackets are ultimately attached to the teeth to be treated so that an orthodontic alignment wire may be applied to the teeth by engagement with the attached brackets.

Apparatus for attaching the brackets to the model teeth includes a support structure for holding a jaw model containing the teeth and a curved alignment table extending at least partially about the jaw holder. A plurality of elongated alignment elements are displaceably mounted upon the alignment table for movement toward and away from the teeth and by adjustable manipulation of the alignment elements the brackets, which are adapted to engage the ends of the alignment elements may be affixed to the model teeth.

11 Claims, 16 Drawing Figures

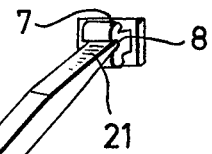
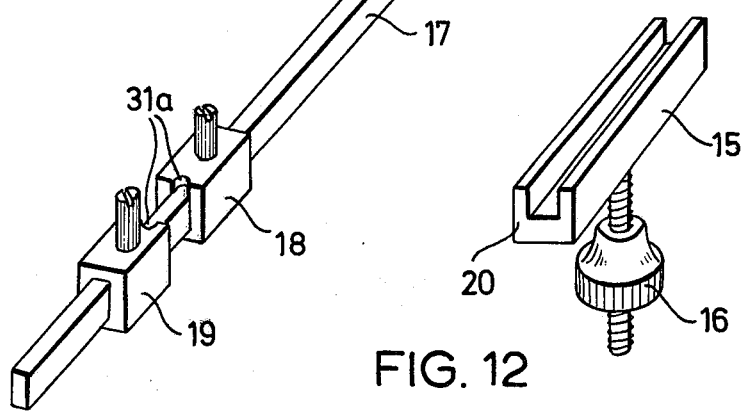
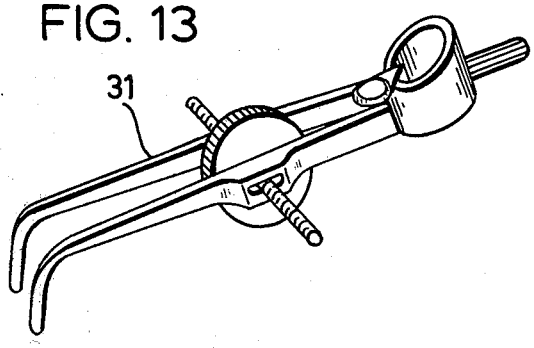

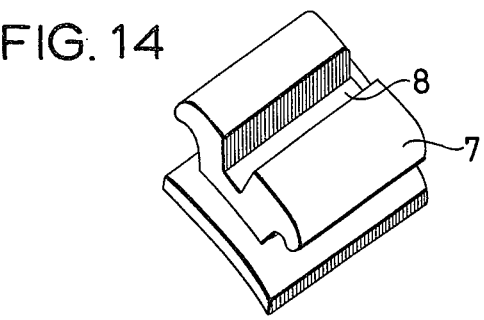
FIG. 14
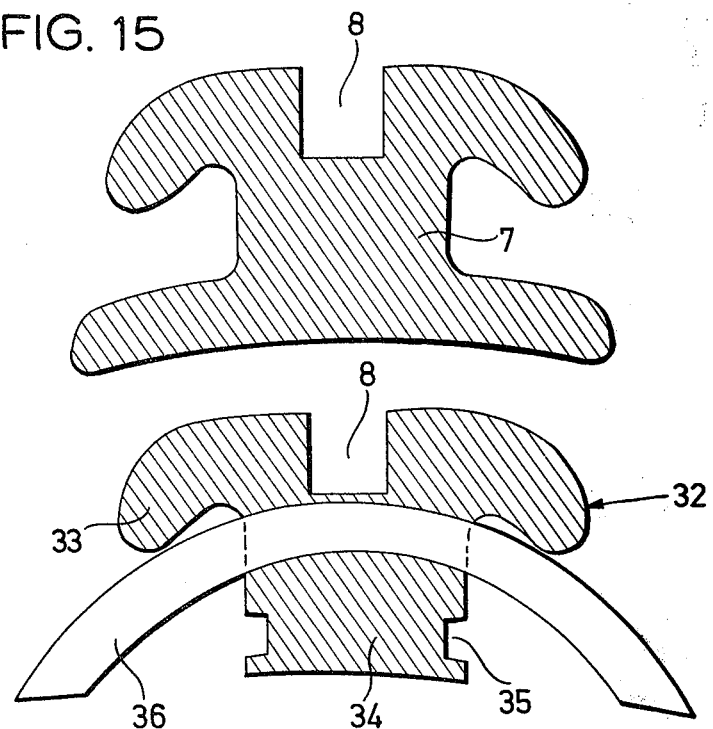
FIG. 15
FIG. 16

PROCESS AND APPARATUS FOR FITTING ORTHODONTIC BRACKETS TO TEETH

BACKGROUND OF THE INVENTION

The present invention relates generally to the laboratory preparation of orthodontic devices and more particularly to the fitting of brackets upon teeth to be orthodontically treated. Furthermore, the invention involves the utilization of positive jaw models in effecting the proper adjustment and positioning of the brackets. The invention also involves the utilization of negative molds of tooth and jaw structures which may be prepared from the positive jaw models and which may be utilized to apply the orthodontic brackets onto the teeth to be treated by means of appropriate dental cement or other similar adhesive.

A known prior art procedure which is related to the present invention is disclosed in a trade publication entitled "Informationen auf Orthodontie und Kieferothopadie", Jan. 1973 issue, pp. 45 ff. A very important factor in the practice of procedures of this type is the precise and correct placement of brackets upon teeth of a positive jaw model which is utilized in the bracket-fitting procedure. This requirement exists as well in formerly known procedures wherein the fitting is formed without a model because it effects the precise and proper fitting of the brackets to the teeth which are to be ultimately treated. The placement and positioning of the brackets upon the teeth must be carefully performed and the procedures must be compatible with the implements which are utilized and with the overall apparatus by which such procedures are performed. If adjustment is to be accomplished with so-called tension arcs, wherein an arc wire is elastically deformed to conform with the orientation of an uneven row of teeth, the success of the treatment procedure depends particularly upon the proper placement and angular positioning of the orthodontic brackets upon each individual tooth. Once a bracket has been fitted upon a respective tooth, its position cannot be changed until the completion of the treatment process. Therefore, if tensioned arcs are to be used, the brackets must be adjusted in such a way that the arc which is finally utilized, which may have a square cross-sectional configuration, will extend through corresponding square slots of each of the brackets without deviation or twist. Thus, the stretching of the tensioned arcs must occur in an appropriate manner and the overall system must accommodate the use of different tensioned arcs of increasingly heavier gauge which are periodically replaced after initiation of the treatment process.

Usually, the procedures which are involved require that tensioned arcs having a generally rounded cross-sectional configuration be used initially and that replacement of the arcs be effected until, finally, a heavier gauge arc of generally square cross-sections is used. In order to comply with these requirements in a manner which achieves placement of the brackets upon the teeth to be treated as precisely as possible, it has hitherto been known to use a plurality of brackets of differing designs with regard to the angular positioning of the bracket slots and bracket feet, due to the fact that the bracket slots must conform on the adjusted denture to an ideal course or path not only with regard to the horizontal course of the arc, but also with regard to their vertical surfaces. This occurs without regard to the fact that the teeth may be of different volumes. The ideal course of the tensioned arc results from a line which may be drawn through the exit points of the imaginary tooth axes on the crowns of the teeth of a sound denture. However, in view of the fact that individual teeth project with marked differences from this ideal tooth arc line, the feet of the brackets must present a correspondingly different spacing from the brackets slots if the slots are to extend parallel to the ideal line of the tooth arc.

Despite the fact that scientific research has made commercially available an assortment of brackets which are designed to correspond to the characteristics of individual teeth, the orthodontic practitioner must nevertheless encounter the difficult task of properly evaluating individual teeth in order to fit the appropriate bracket in each given case with a correct positioning on the tooth. A projected view of the imaginary axis of the teeth plays an essential role within the context of an assessment of such imaginary axis. This relates to the corrected overall position of the still uncorrected dentures. Even though the procedures described above are facilitated to some extent by the fact that positive jaw models may be utilized, problems will nevertheless occur just as the case where brackets are directly fitted to the teeth in the mouth.

Accordingly, the present invention is directed toward substantially facilitating the fitting of brackets to the teeth of a positive jaw model. The invention obviates the need for complicated measurements and calculations as well as the selection of multiple brackets of different shapes. Furthermore, the invention is directed toward mechanization or standardization of the laboratory preparation and fitting of the brackets to the teeth in such a manner that the work may be performed as a more or less routine procedure even by personnel which do not have highly specialized training in the field.

SUMMARY OF THE INVENTION

Briefly, in one aspect thereof, the present invention may be described as a process for attaching brackets to teeth which are to be orthodontically treated comprising the steps of forming a first positive jaw model as a replica of the jaw containing said teeth to be orthodontically treated, said first jaw model being formed with replaceably removable model teeth which are replicas of the teeth to be treated. The replaceable model teeth are removed from the first jaw model and transferred to a second jaw model which is composed of pliable material capable of enabling adjustable positioning of the model teeth therein. Subsequently, the model teeth are adjusted in the second jaw model to effect a desired orientation thereof which is a replica of the tooth orientation which is ultimately desired for the teeth which are to be treated. With the teeth in their desired orientation, orthodontic brackets are attached to the model teeth and the model teeth are subsequently replaced with the brackets attached into the first jaw model. A negative mold of the teeth with the attached brackets is then made and by use of the negative jaw model, the brackets are subsequently affixed, by cementing or the like, upon the teeth to be ultimately treated.

The present invention also provides apparatus for securing the orthodontic brackets upon the model teeth while the model teeth are in their desired orientation in the second jaw model. Briefly, the apparatus of the present invention may be described as comprising holder means adaptable to have a jaw model containing the model teeth supported thereon, means for adjusting the position of the holder means including means for adjustably vertically displacing the holder means, a curved alignment table extending at least partially about the holder means in a substantially horizontal plane, a plurality of guide members mounted on the alignment table and adapted to be adjustably positioned thereon in directions extending generally circumferentially about the jaw model, said guide members also being rotatably adjustable about a vertical axis, and an elongated alignment element supported upon each of the guide members for adjustable horizontal displacement toward and away from the teeth to enable attachment of the brackets to the teeth in a desired orientation. The apparatus is configured to enable provision therein of one alignment member and an associated guide member for each of the teeth upon which a bracket is to be attached and the alignment members have their ends closest to the teeth formed so that they will engage the slots of the brackets which are to be attached. Each of the alignment members have mounted thereon a pair of adjustable stop members which enable proper alignment and positioning of the alignment members and brackets during the fitting process.

In the attachment of the brackets to the model teeth, the brackets are arranged so that the slots formed therein will extend tridimensionally parallel to an ideal line of the arc utilized in the orthodontic procedure. The tensioned arcs may then be applied to extend through the slots thereby operating to effect the desired orthodontic tooth alignment.

The various features of novelty which characterize the invention are pointed out with particularity in the claims annexed to and forming a part of this disclosure. For a better understanding of the invention, its operating advantages and specific objects attained by its use, reference should be had to the accompanying drawings and descriptive matter in which there are illustrated and described preferred embodiments of the invention.

DESCRIPTION OF THE DRAWINGS

In the drawings:

FIG. 11 is a perspective view of an alignment element utilized in the apparatus of the present invention;

FIG. 12 is a perspective view of a guide member utilized in the apparatus of the present invention;

FIG. 13 is a perspective view of an adjustment compass utilized with the apparatus of the present invention;

FIG. 14 is a perspective view of a standard orthodontic bracket;

FIG. 15 is a sectional view on an enlarged scale of the orthodontic bracket of FIG. 14; and FIG. 16 is a sectional view illustrating a different orthodontic bracket which may be utilized with the present invention.

DETAILED DESCRIPTION OF THE PREFERRED EMBODIMENTS

Figure 1:
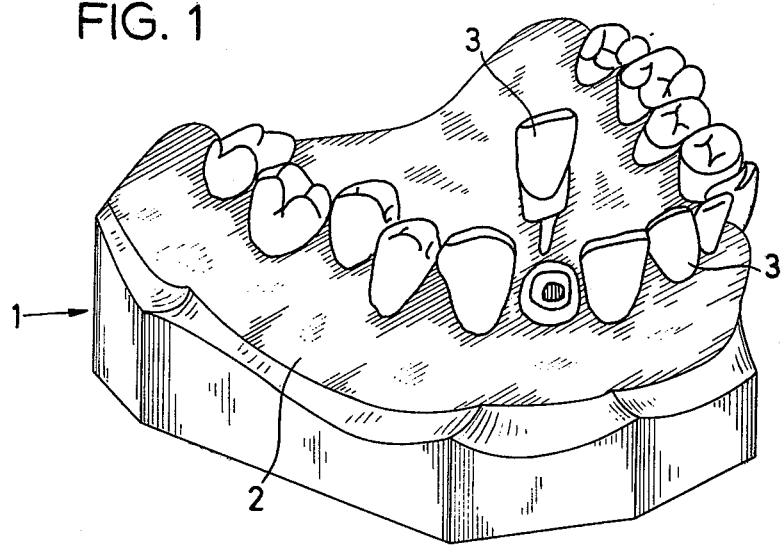
FIG. 1 is a perspective view of a first positive jaw model having therein replaceably removable teeth which are replicas of the teeth to be treated.

The method of the present invention may be described by reference to FIGS. 1–8 which illustrate various implements utilized in the conduct of the procedures of the invention. FIG. 1 illustrates a first positive jaw model 1 which is prepared at the beginning of the treatment procedures and which includes a jaw section 2 made of rigid model material such as plaster of Paris. The model 1 includes a plurality of replaceably removable teeth 3 which also may be made of rigid material such as plaster of Paris, which teeth are replicas of teeth of a human mouth which are to be orthodontically treated. The orientation of the teeth 3 as shown in FIG. 1 conforms to the orientation of a set of real teeth prior to application of the orthodontic treatment thereto.

The model shown in FIG. 1 involves the use of dowel pins which enable removal and replacement of the teeth, and such a model may be made utilizing known dental techniques available to those skilled in the art. Accordingly, details of the manufacture of this model are not necessary to a complete understanding of the present invention and are not set forth herein.

Figure 2:
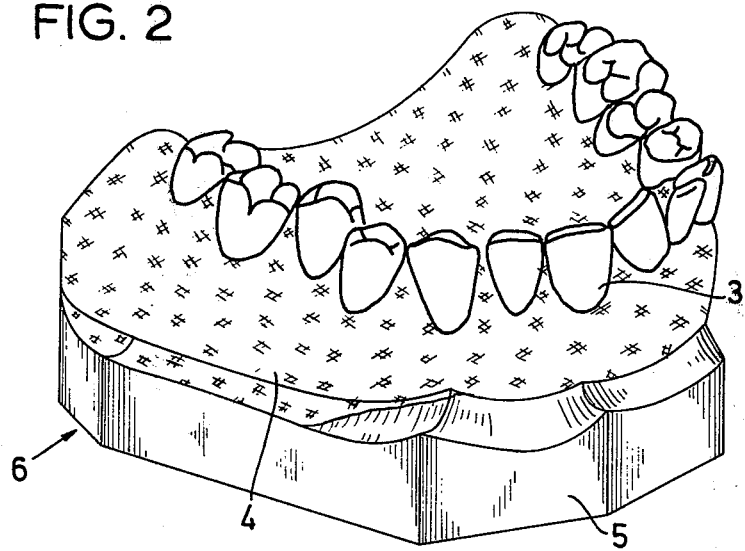
FIG. 2 is perspective view of a second jaw model utilized in the process of the present invention having the removable model teeth of the first jaw model applied therein.

Following completion of the model in accordance with FIG. 1, the model teeth 3 are removed therefrom and are inserted into a second jaw model previously prepared and shown in FIG. 2. In the preparation of the second jaw model the teeth may be removed from the model shown in FIG. 1 and inserted into a negative jaw model prepared beforehand for producing the positive jaw model or into a doubling negative prepared separately according to the layout model, and the jaw area is subsequently filled with wax for the formation of a complete positive model, in which process, in order to achieve improved handling, the balance of the hollow mold following solidification of the wax is filled with plaster of Paris so as to achieve a stable base of the three-layer compound model produced in this manner which is shown in its finished form in FIG. 2. Thus, a second jaw model 6, shown in FIG. 2, has therein the model teeth 3, which are the same teeth as those shown in the model of FIG. 1, while a jaw area 4 accommodating the model teeth therein consists of wax, with a base plate 5 consisting of a model material having the same hardness as the entire jaw part 2 in the case of the model according to FIG. 1.

Figure 3:
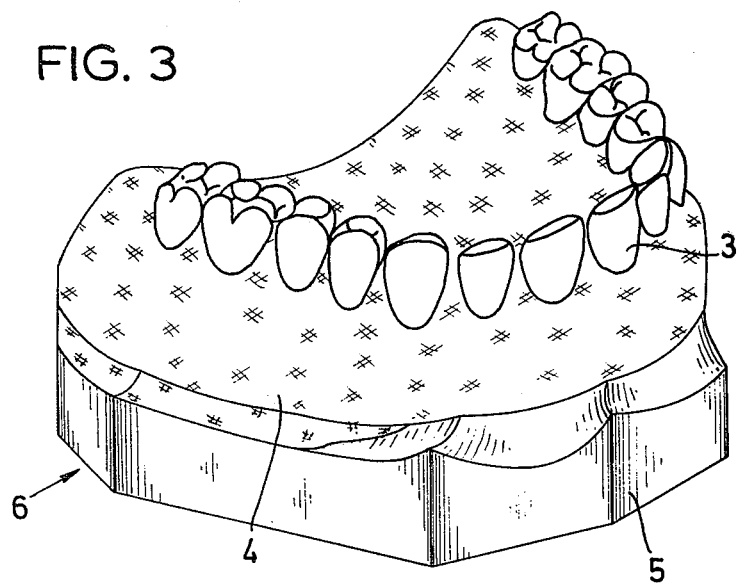
FIG. 3 is a perspective view of the second jaw model showing the model teeth in their optimally aligned or idealized orientation.

In a subsequent step of the procedure, the wax of the jaw area 4 of the model 6 is brought to a plastic or pliant state by application of heat thereto. Alternatively, there may be used wax or other suitable material that is sufficiently pliant at room temperature to enable movement of the teeth 3 therein. With the jaw area 4 in a sufficiently pliant state, the model teeth 3 are moved or adjusted so that they will be placed into a desired orientation which duplicates, essentially, the idealized orientation which is ultimately desired in the teeth to be orthodontically treated. The idealized orientation of the model teeth is shown in FIG. 3 wherein there is depicted the second jaw model 6 after the teeth 3 have been placed in their desired orientation while the jaw area 4 is in a sufficiently pliant state. This operation may be performed in a so-called "articulator" and corresponds in a practical sense to the mode of operation used in the preparation of a tooth prosthesis.

Figure 4:
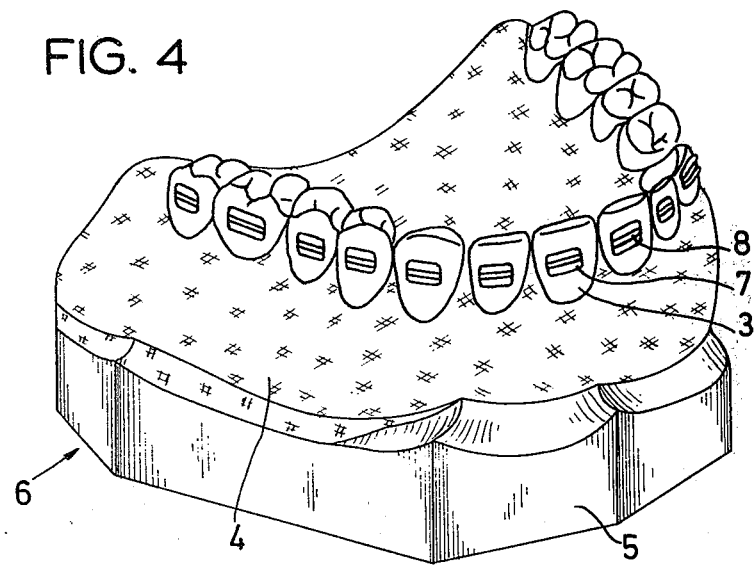
FIG. 4 is a perspective view showing the model teeth of FIG. 3 after orthodontic brackets have been attached thereto.

Subsequently, the model 6 with its teeth aligned in an ideal position in accordance with FIG. 3, and following adequate cooling of the wax substance in order to prevent undesirable subsequent shifting of the teeth, is inserted in the apparatus of the present invention depicted in FIGS. 9–14 in order to provisionally affix the brackets to the model teeth while the model teeth are in their desired orientation. The apparatus and procedures utilized in affixing the brackets to the model teeth will be described in greater detail hereinafter. FIG. 4 shows the model 6 with the solid model teeth in their ideal position and with brackets 7 provisionally cemented thereon, with bracket slots 8 of the brackets 7 being arranged parallel to the ideal tooth arc line.

Figure 5:
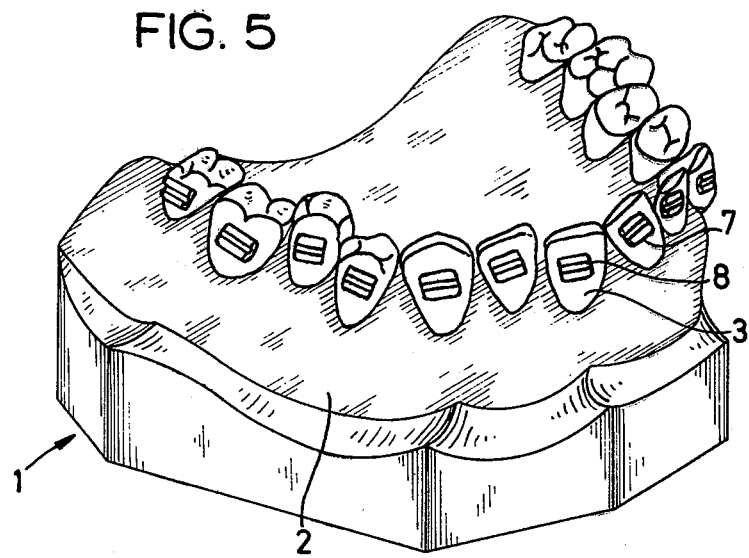
FIG. 5 is a perspective view of the first jaw model after the model teeth with brackets attached thereto have been replaced therein.

The solid model teeth 3 with their brackets 7 are removed from the wax jaw area 4 during the subsequent phase of the process of the present invention and they are reinserted into the jaw area 2 of the model shown in FIG. 1 which is made of hard model material and from which they had been removed initially. This stage of the operation is depicted in FIG. 5 which shows the original or first jaw model 1 having the teeth 3 replaced therein in their original position except that the teeth now have the brackets 7 affixed thereto.

Figure 6:
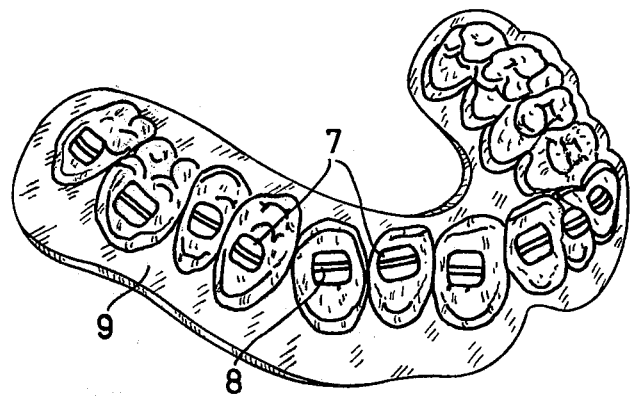
FIG. 6 is a perspective view of a negative mold made of plastic material from the model of FIG. 5 which serves as a transfer mask for the brackets enabling the brackets to be trnsferred from the model teeth to the teeth to be orthodontically treated.

Subsequent phases of the process of the present invention generally correspond to processes known in the art and they will be briefly described hereinafter for purposes of a better understanding of the present invention. From the model shown in FIG. 5 there is prepared a negative mold 9 made of elastic material, preferably a plastic sheet and appropriately formed by means of a suitable deep-drawing device in which process the brackets 7 that have been only provisionally attached to the model teeth become adherent within the negative mold 9 as illustrated in FIG. 6.

Figure 7:
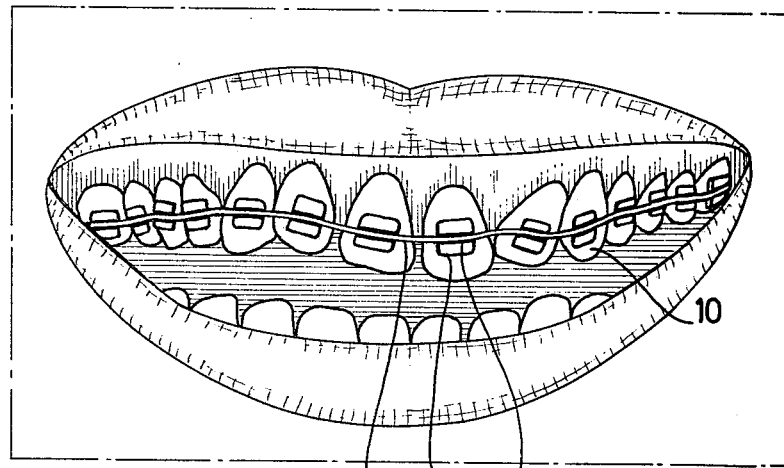
FIG. 7 is a schematic front view showing a representation of the human mouth having the teeth therein with brackets applied and with a tension arc wire extending through the slots of the brackets, the teeth being shown in their orientation at the beginning of the orthodontic treatment procedure.
Figure 8:
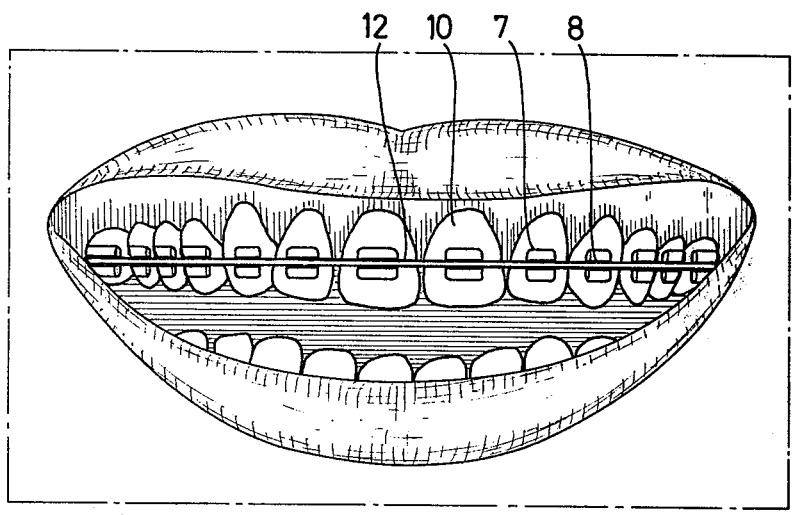
FIG. 8 is a schematic front view representing the human mouth of FIG. 7 showing the teeth at the completion of the orthodontic treatment procedure with a square wire arc arranged in the slots of the brackets.

In this manner, a transfer mask may be formed by means of which the brackets 7 may be applied onto the real teeth 10 within a human mouth and attached thereto by means of a suitable permanent cement, as illustrated in FIG. 7. After attachment of the brackets 7 upon the real teeth 10, there is inserted into the slots 8 of the brackets 7 an initial, comparatively thin round alignment wire arc 11 attached in an adequate manner by means of tie pieces engaging beneath the lobes of the brackets. In the course of the treatment increasingly thicker wire arcs are used until, eventually, there is inserted into the slots of the brackets a square wire arc 12 which is exactly fitted to the shape of the slots and which eventually assumes a completely stretched path, as illustrated in FIG. 8. As a result of this, the natural teeth will have assumed the ideal position of the model teeth 3 depicted in FIG. 4 and the active part of the treatment may be terminated.

Thus, as will be apparent from the foregoing, when the brackets are first attached to the model teeth 3, the model teeth are in an idealized position or desired orientation as depicted in FIG. 4. Since the brackets 7 are attached with the model teeth in their desired orientation, the brackets will, when subsequently affixed to natural teeth, tend to reestablish the idealized orientation which was maintained during initial application of the brackets 7 to the model teeth. Thus, the desired orthodontic results depicted in FIG. 8 may thus be accomplished.

The provisional attachment of the brackets 7 to the model teeth 3 in their ideal position in accordance with the arrangement of FIG. 4 is accomplished by utilization of the apparatus of the present invention which will be described in greater detail by reference to FIGS. 9–13 which depict this apparatus.

The apparatus of the present invention essentially consists of a substantially U-shaped alignment table 13 having a corresponding U-shaped central longitudinal slot 14 along which there is provided a number of guide members 15 that are longitudinally displaceable and which can be fixed by means of a corresponding setscrew 16 at any desired position. Each of the guide members 15 may be adjustably positioned along the length of the slot 14 and they may also be rotated about a vertical axis corresponding with the central axis of the setscrew 16. It will be noted that the alignment table 13 extends in a generally horizontal plane with a curved configuration. Within each of the guide members 15 there is arranged an alignment element 17 which may be longitudinally displaced within the guide member 15. At the outer extremity of each of the alignment elements 17 there are arranged a pair of displaceable and settable stop members 18 and 19 of which the inner stop member 18 cooperates with a corresponding stop surface 20 formed on the guide element 15 and associated therewith. The inner extremity or tip 21 of each alignment element 17 is designed to accommodate or to carry a bracket 7 by engagement within the slots 8.

In the central portion of the apparatus, there is mounted a model holder 22 having a ball-and-socket joint 23 formed therewith in such a manner that the model holder 22 may be set in any special position by means of a setting screw 24. The ball joint 23 is arranged upon a plate 26 which is vertically displaceable along the vertical support 25 and which is adjustable with regard to its vertical elevation by a screw 28 having a threaded exterior guided in a stationary plate 27 by means of a handwheel 29.

In the operation of the apparatus of the present invention, the model 6 shown in FIG. 4 is first attached to the model holder 22 and subsequently the masticating plane of this model is aligned on the horizontal alignment table 13 by means of the ball-and-socket joint 23. Thereupon, the model is lowered by means of the handwheel 29 to an extent such that an alignment element 17 which may be slidingly moved within a guide member 15 will just clear the masticating surface or the cutting edge of the related tooth model 3. A tip 21 of the alignment element 17 is then aligned with an imagined ideal tooth arc line 30. Thereupon, the tooth stop members 18 and 19 are brought into engagement with each other and the stop 18 is brought into abutment with the stop surface 20 on the guide member 15. The outer stop members 19 are set in place by tightening of the set screws thereof, with the set screws of the stop members 18 being retained in their untightened condition.

Figure 9:
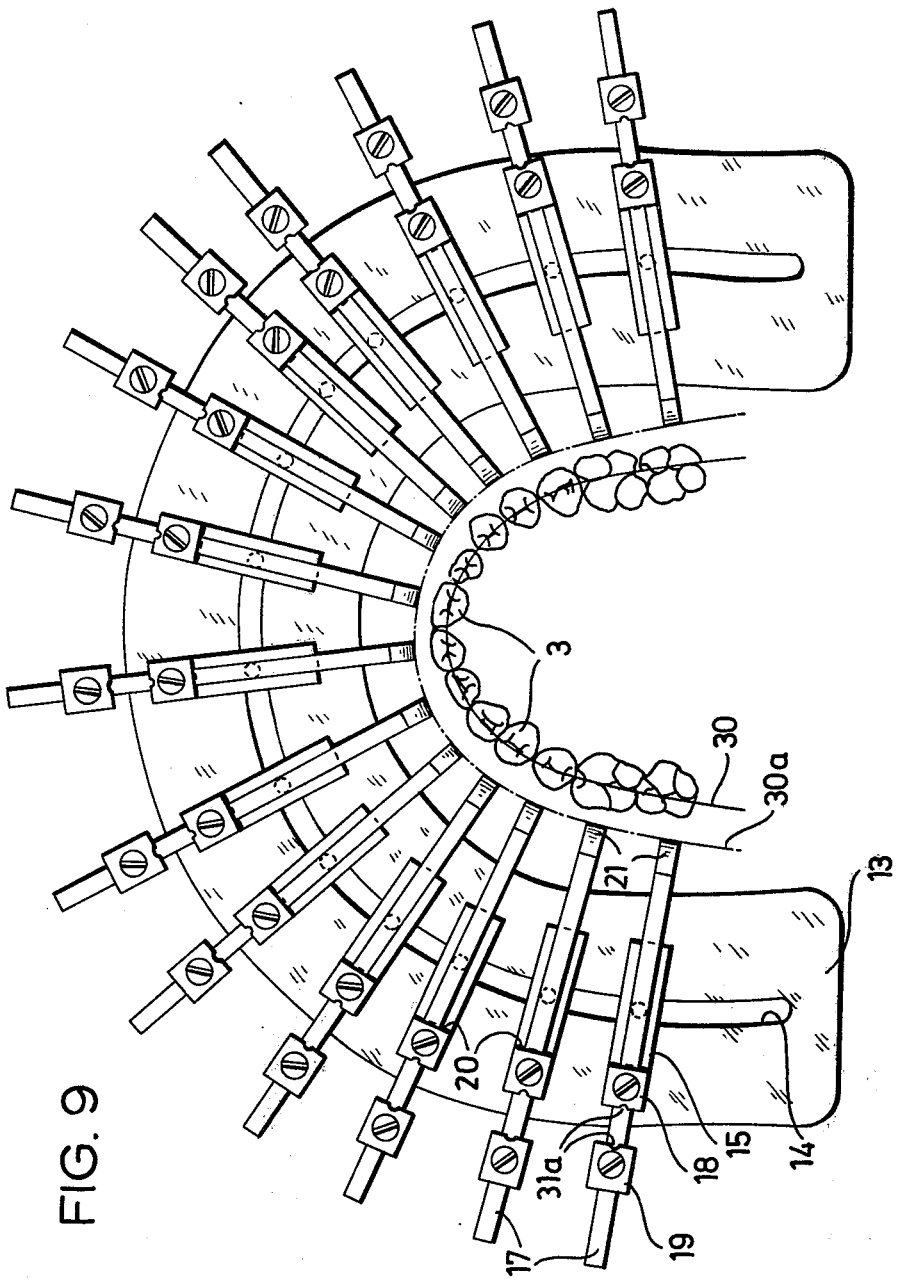
FIG. 9 is a top view of the apparatus of the present invention which is utilized in the placement of the orthodontic brackets upon the model teeth.
Figure 10:
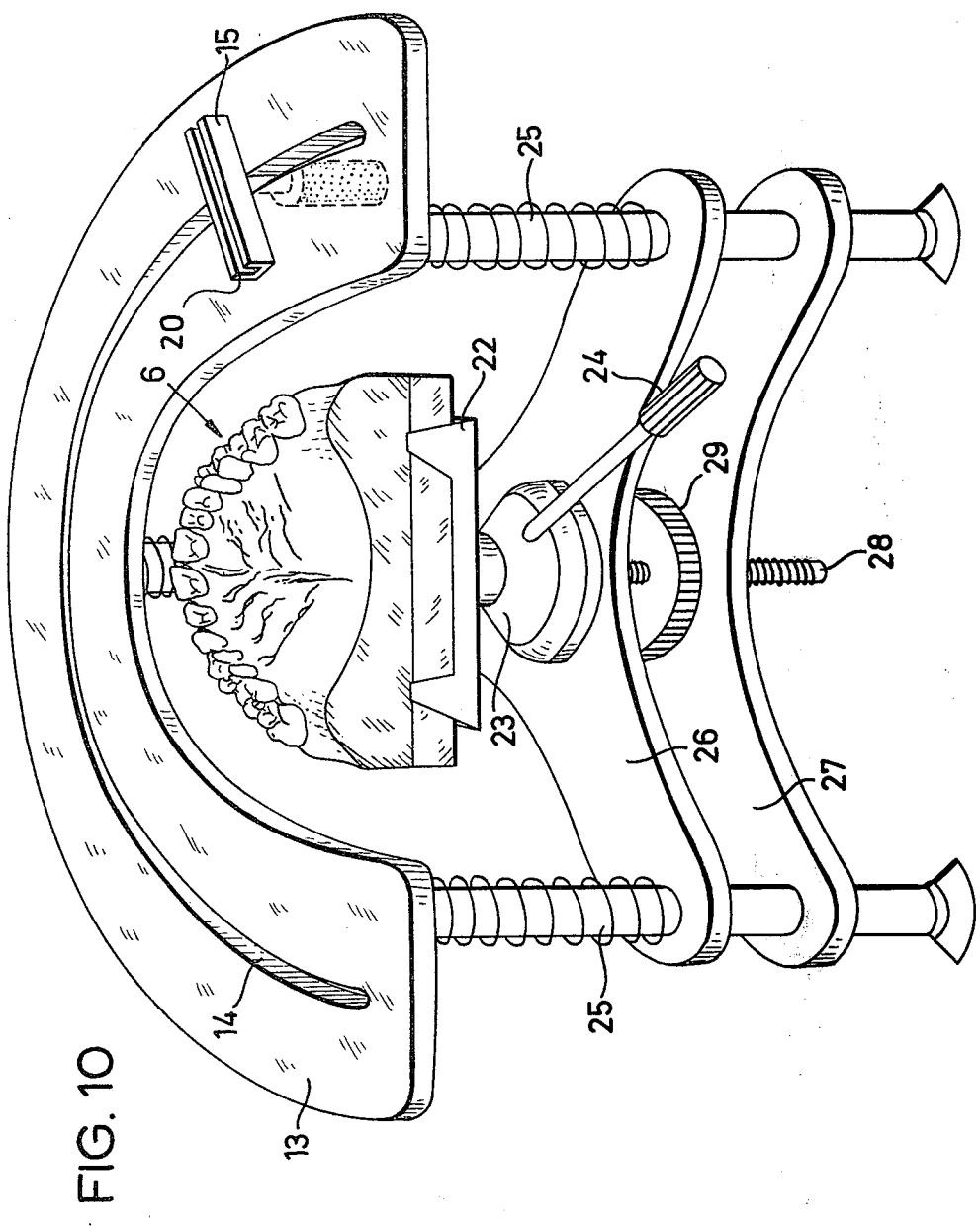
FIG. 10 is a perspective view of the apparatus shown in FIG. 9.

As best seen in FIG. 9, the alignment table 13 extends at least partially about the jaw model 6 and there is provided one alignment element 17 with an associated guide member 15 for each tooth of the teeth of the jaw model 6.

After the alignemnt element 17 corresponding to each tooth model 3 has been set in this position, all of the alignment elements 17 are withdrawn and the model 6 is raised until the tips of the alignment elements are positioned and directed at a theoretical line of the bracket slots 8 which is situated at about one half the elevation of the crowns of the teeth. Thereupon, a determination is made of the spacing of one bracket slot 8 from the tooth arc line 30, governed by the tooth 3 of maximum projection, which is normally the case with permanent molars. For that purpose, a bracket 7 is placed onto the tip 20 of the alignment element 17 intended for the particular permanent molars, and the alignment element is pushed toward the tooth to the extent permitted by the bracket. Thereupon, the inner and still unfastened stop 18 is again advanced toward the stop 20 of the corresponding guide member 15 and is secured in place by tightening of its setscrew.

It will be noted that, as a result of this procedure, a spacing will exist between the two stop members 18 and 19. This spacing is then measured by means of an adjustable compass 31 which is shown in FIG. 13. For this purpose, the two stop members 18 and 19 are provided at their opposed facing sides with recesses 31a which are adapted to have engaged therein the tips of the compass 31. Thus, by utilization of the compass 31, a corresponding spacing may be set between the stop members 18 and 19 of all the other alignment elements 17.

Subsequent to the completion of these procedures, all the alignment elements may be moved to approach the model teeth just far enough that the tips 21 of the alignment elements or the slots 8 of the brackets 7 situated thereat, form a line 30a extending parallel to the ideal line 30 of the tooth arc, with all the bracket slots being arranged in a horizontal plane, as shown in FIG. 9.

Connecting of the brackets 7 is accomplished through underlining of the bracket bases or feet. For that purpose, there is preferably used a high quality self-polymerizing acrylate. The foot of the bracket is provided with an adequate amount of the plastic mixture of this self-polymerizing material and then the bracket is placed on the tip of a particular alignment element 17 and is advanced by pushing the alignment element forwardly to the tooth which has been previously insulated. The stop member 18 determines the desired space from the tooth so that a bracket foot of corresponding thickness is formed individually at each tooth in accordance with the projection of the respective tooth with respect to the ideal line of the tooth arc. That is, it is molded to fit precisely on the tooth which is of particular advantage for the subsequent final cementing to the corresponding tooth in the mouth.

After all the brackets have been fitted in this manner and the acrylate lining has cured, which requires approximately 15 minutes, the brackets may be marked in their position with respect to the masticating surface or the cutting edge, taken off one after the other from the alignment elements and inserted after sorting into a so-called "tooth rack" or "tooth fan screen" to prevent any misplacement thereof.

Subsequently there follows separating of the excess lining material, a procedure which is familiar to the dental technician skilled in the art, during which the foot of the bracket can be adjusted more precisely to the dimensions of the respective tooth.

By means of the alignment element 17, the brackets provided with an ordinary cement that can be washed off, are placed once again against the teeth or pushed again toward them and are provisionally attached. The brackets 7 need adhere to the model teeth 3 only to such an extent that their position is secured until they are incorporated into the transfer mask 9 in accordance with the arrangement depicted in FIG. 6.

The lining hereinbefore described may, in principle, be used with any brackets available on the market, of which a sample bracket 7 having a slot 8 is depicted in FIGS. 14 and 15.

A bracket particularly preferred for the mode of operation in accordance with the present invention is a bracket 32 depicted in FIG. 16. This bracket corresponds in its area averted from the tooth to a standard design with a slot 8 and vanes or lobes 33. The bracket has, however, a foot 34 having formed therein undercuts 35 with a cup-shaped molded element 36 being pushed or applied over the foot 34. The molded element 36 is preferably made of an elastic plastic material and comprises a central aperture corresponding to the shape of the foot of the bracket. The thickness of the molded section 36 is such that, upon later removal thereof, that is, following the insertion of the material which serves as the lining, there is available a sufficient gap between the molded-on bracket foot and the bracket vanes or lobes 33 to permit attachment of thinner tensioning arc wires by means of the lobes 33.

It will be seen that in the case of a bracket of this design, the bracket itself may be made of any material, even of a material that does not enter into a polymerization bond with the lining material, in view of the fact that the undercuts 35 provide in any event an adequate linkage. As a result, the bracket may consist wholly of metal or else only a U-shaped area surrounding the slot 8 may be made of metal. This may be the case, for example, if certain brackets must absorb particularly high leverages exerted by the wire arcs which are inserted in their slots.

The mode of operation in accordance with the present invention, and the devices and brackets utilized for this purpose, may differ in many respects from the specific description provided herein without departing from the underlying concepts of the invention. Thus, as already has been suggested, there may be used in lieu of wax for the jaw model 6 according to FIGS. 2–4 of a suitable material which may, for example, comprise materials that do not require heating or materials which are sufficiently dimensionally stable to prevent undesirable shiftings of the teeth once the ideal position thereof in the model has been achieved. The shape of the brackets used in the mode of operation in accordance with the present invention may likewise be adapted to particular requirements.

Thus, it will be seen that the procedures according to the present invention are intended to cause the model teeth to achieve a desired ideal position or orientation in a material which is suited for this purpose and which enables alignment of the brackets with their slots parallel to an ideal line of the arc of the teeth. In the alignment of the brackets the slots are oriented to extend tridimensionally to the ideal line of the arc of the teeth. Complicated measurements and theoretical precalculations may be dispensed with and the fitting of the brackets on the model teeth may be performed in a standardized or uniform procedure in such a way that the operations may be performed by personnel having a lesser degree of specialized training.

In the practice of the present invention, it is particularly advantageous to achieve, upon fitting of the brackets in their ideal position to the model teeth, a fitting of correspondingly exact shape of the bracket foot by lining it beneath by means of materials suitable for the material of the bracket. This mode of operation makes it possible to suitably use in practice one single type of bracket or a limited number of types of brackets attended by the additional advantage that there is guaranteed in any event a completely accurate fitting of the bracket foot to the related tooth. That is to say, there may be obtained substantially better results than are obtained in the case of procedures utilizing a large number of brackets with differently shaped bracket feet which have heretofore been available. Thus, there is enabled a substantial improvement in the subsequent or final cementing of the brackets to the natural teeth.

Furthermore, in the practice of the invention it is particularly recommended to impart to the molding section that is removable following curing of the lining material a thickness corresponding to that of the gap required between the bracket lobes or hooks and the bracket foot in such a way that the molded section obtains through the bracket lobes or hooks a satisfactory bracing in its molded position.

While specific embodiments of the invention have been shown and described in detail to illustrate the application of the inventive principles, it will be understood that the invention may be embodied otherwise without departing from such principles.

What is claimed is:

1. A process for attaching orthodontic brackets to teeth to be orthodontically treated comprising the steps of forming a first positive jaw model as a replica of a jaw containing said teeth to be treated, said first jaw model being formed with replaceably removable model teeth which are replicas of said teeth to be treated, transferring said model teeth to a second jaw model composed of pliable material capable of enabling adjustable positioning of said model teeth therein, adjusting the positions of said model teeth in said second jaw model to effect a desired orientation thereof, said desired orientation being a replica of the tooth orientation ultimately desired for said teeth to be orthodontically treated, attaching to said model teeth orthodontic brackets while said model teeth are in said desired orientation, replacing said model teeth with said brackets attached thereto within said first positive jaw model, and transferring said brackets from said model teeth to said teeth to be orthodontically treated by utilizing said first jaw model to form a negative mold of said model teeth and brackets and subsequently utilizing said negative mold as a transfer mold to attach said brackets to said teeth to be orthodontically treated.

2. A process according to claim 1 wherein said brackets include foot portions to which said brackets are attached to said model teeth, said process being performed so that upon application of said brackets in a desired position upon said model teeth there is effected a true fit of said bracket foot portions by underlining by means of material suited for the material of said brackets.

3. A process according to claim 1 wherein said orthodontic brackets comprise slots adapted to have inserted therein an orthodontic alignment wire, said brackets being attached to said model in such a position that said slots are oriented to extend tridimensionally parallel to an ideal line of the tooth arc of said model teeth while in said desired orientation.

4. Apparatus for securing orthodontic brackets to model teeth comprising holder means adapted to have a jaw model containing said teeth supported thereon, means for adjusting the position of said holder means including means for adjustably vertically displacing said holder means, a curved alignment table extending at least partially about said holder means in a substantially horizontal plane, a plurality of guide members mounted on said alignment table and adapted to be adjustably positioned thereon in directions extending generally circumferentially about said jaw model, said guide members also being rotatably adjustable about a vertical axis, and elongated alignment elements supported upon said guide members for adjustable horizontal displacement toward and away from said teeth to enable attachment of said brackets to said teeth in a desired orientation, said apparatus being configured to enable provision therein of one alignment element and an associated guide member for each of said teeth upon which a bracket is to be attached.

5. Apparatus according to claim 4 wherein each of said alignment elements is mounted for sliding engagement in one of said guide members to extend longitudinally from one of said model teeth, with each of said alignment elements including a pair of stop members adjustably affixed thereto both located on one side of said guide member, with one of said stop members being adapted to be brought into abutment with said guide member to enable desired positioning of said alignment element relative to said model tooth.

6. Apparatus according to claim 5 wherein each of said alignment elements comprise a pair of ends with one of said ends being adapted to be located proximate one of said model teeth, said one end being configured to have one of said brackets supported thereupon.

7. Apparatus according to claim 6 wherein each of said brackets includes a slot defined thereon, said slot being adapted to have engaged therein a tensioned wire arc during the performance of an orthodontic treatment, said one end of each of said aligment members being configured to be engaged within one of said slots to enable mounting of said brackets upon said model teeth in an orientation enabling a desired alignment of said slots.

8. Apparatus according to claim 4 wherein each of said brackets comprises a foot portion adapted to facilitate mounting of said bracket to a tooth, said foot portion including undercuts, said apparatus further comprising a molded section enabling underlining of said foot portion with materials universally surrounding said foot portion.

9. Apparatus according to claim 8 wherein said bracket includes lobes located on a side of said bracket opposite said foot portion, said molded section being configured to be removably mounted on said bracket between said foot portion and said lobes and to be removable therefrom after curing of said underlining material, said molded section having a thickness corresponding to a predetermined spacing desired between said lobes and said foot portion.

10. Apparatus according to claim 8 wherein said bracket consists essentially in its entirety of metallic material.

11. Apparatus according to claim 7 wherein said bracket comprises a U-shaped portion consisting essentially of metallic material surrounding said slot.

* * * * *